(12) United States Patent
Wu et al.

(10) Patent No.: US 7,223,341 B2
(45) Date of Patent: *May 29, 2007

(54) POSITIVELY CHARGED MEMBRANE

(75) Inventors: Xiaosong Wu, Pensacola, FL (US);
Chung-Jen Hou, Pensacola, FL (US);
Jayesh Dharia, Pensacola, FL (US);
Peter Konstantin, Boulder, CO (US);
Yujing Yang, Newton, MA (US)

(73) Assignee: Pall Corporation, East Hills, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/480,977

(22) Filed: Jul. 6, 2006

(65) Prior Publication Data
US 2006/0249445 A1   Nov. 9, 2006

Related U.S. Application Data

(63) Continuation of application No. 11/035,950, filed on Jan. 18, 2005, now Pat. No. 7,094,347, which is a continuation of application No. 10/891,098, filed on Jul. 15, 2004, now Pat. No. 6,851,561, which is a continuation of application No. 09/914,163, filed as application No. PCT/US00/04786 on Feb. 25, 2000, now Pat. No. 6,780,327.

(60) Provisional application No. 60/121,670, filed on Feb. 25, 1999, provisional application No. 60/121,669, filed on Feb. 25, 1999.

(51) Int. Cl.
*B01D 39/14*   (2006.01)
*B01D 63/00*   (2006.01)

(52) U.S. Cl. .................. 210/500.37; 210/500.21; 210/500.35; 210/500.38; 210/500.41; 210/490

(58) Field of Classification Search .................. None
See application file for complete search history.

(56) References Cited

U.S. PATENT DOCUMENTS 3,847,652 A   11/1974   Fletcher et al.

(Continued)

FOREIGN PATENT DOCUMENTS

EP   0 008 945   3/1980

(Continued)

OTHER PUBLICATIONS

House, D. A., et al., *Inorganic Chemistry*, 5(12):2097-2102 (1966).

(Continued)

*Primary Examiner*—Krishnan S. Menon
(74) *Attorney, Agent, or Firm*—Leydig, Voit & Mayer, Ltd.

(57) ABSTRACT

The present invention provides a positively charged microporous membrane having a protein binding capacity of about 25 mg/ml or greater comprising a hydrophilic porous substrate and a crosslinked coating that provides a fixed positive charge to the membrane. The present invention further provides a positively charged microporous membrane comprising a porous substrate and a crosslinked coating comprising pendant cationic groups. The membranes of the present invention find use in a variety of applications including ion-exchange chromatography, macromolecular transfer, as well as detection, filtration and purification of biomolecules such as proteins, nucleic acids, endotoxins, and the like.

16 Claims, 3 Drawing Sheets

U.S. PATENT DOCUMENTS

| | | | |
|---|---|---|---|
| 3,992,495 A | 11/1976 | Sano et al. |
| 4,101,461 A | 7/1978 | Strop et al. |
| 4,111,858 A | 9/1978 | Kostrzewa et al. |
| 4,242,208 A | 12/1980 | Kawaguchi et al. |
| 4,246,355 A | 1/1981 | Bolto et al. |
| 4,250,029 A | 2/1981 | Kiser et al. |
| 4,311,799 A | 1/1982 | Miyake et al. |
| 4,360,434 A | 11/1982 | Kawaguchi et al. |
| 4,380,590 A | 4/1983 | Chong |
| 4,388,189 A | 6/1983 | Kawaguchi et al. |
| 4,473,474 A | 9/1984 | Ostreicher et al. |
| 4,512,896 A | 4/1985 | Gershoni |
| 4,523,995 A | 6/1985 | Pall et al. |
| 4,601,828 A | 7/1986 | Gershoni |
| 4,675,252 A | 6/1987 | Hashimoto et al. |
| 4,690,766 A | 9/1987 | Linder et al. |
| 4,693,985 A | 9/1987 | Degen et al. |
| 4,702,840 A | 10/1987 | Degen et al. |
| 4,708,803 A | 11/1987 | Ostreicher et al. |
| 4,711,793 A | 12/1987 | Ostreicher et al. |
| 4,839,203 A | 6/1989 | Davis et al. |
| 4,915,839 A | 4/1990 | Marinaccio et al. |
| 4,962,140 A | 10/1990 | Diamantoglou |
| 4,980,067 A | 12/1990 | Hou et al. |
| 5,004,543 A | 4/1991 | Pluskal et al. |
| 5,032,281 A | 7/1991 | Nagamatsu et al. |
| 5,085,780 A | 2/1992 | Ostreicher |
| 5,114,585 A | 5/1992 | Kraus et al. |
| 5,128,041 A | 7/1992 | Degen et al. |
| 5,135,650 A | 8/1992 | Hjerten et al. |
| 5,137,633 A | 8/1992 | Wang |
| 5,151,189 A | 9/1992 | Hu et al. |
| 5,178,766 A | 1/1993 | Ikeda et al. |
| 5,232,595 A | 8/1993 | Meyer |
| 5,277,812 A | 1/1994 | Hu et al. |
| 5,282,971 A | 2/1994 | Degen et al. |
| 5,407,581 A | 4/1995 | Onodera et al. |
| 5,520,849 A | 5/1996 | Eiffler |
| 5,547,575 A | 8/1996 | Demmer et al. |
| 5,605,616 A | 2/1997 | Zepp |
| 5,621,088 A | 4/1997 | Gruber |
| 5,707,741 A | 1/1998 | Hoenel et al. |
| 5,759,404 A | 6/1998 | Ericsson et al. |
| 5,770,712 A | 6/1998 | Roy et al. |
| 5,780,616 A | 7/1998 | Fornasari et al. |
| 6,780,327 B1 | 8/2004 | Wu et al. |
| 6,849,185 B1 | 2/2005 | Wu et al. |
| 6,851,561 B2 | 2/2005 | Wu et al. |
| 2005/0211621 A1 | 9/2005 | Wu et al. |

FOREIGN PATENT DOCUMENTS

| | | |
|---|---|---|
| EP | 0 026399 | 4/1981 |
| EP | 0 343 387 B1 | 11/1989 |
| GB | 2 275 626 A | 3/1994 |
| WO | WO 93/10899 | 6/1993 |
| WO | WO 97/33683 | 9/1997 |

OTHER PUBLICATIONS

Spell, H. L., *Analytical Chemistry*, 41(7):902-905 (1969).

Hall, H. K., Jr., *Nucleophilic Aliphatic Amines*, 29:3539-3544 (1964).

Jenkins, A. D., et al., *Pure & Appl. Chem.*, 88(12):2287-2288 and 2297.

Petsch, D. et al., *Journal of Chromatography B*, 693:79-91 (1997).

Petsch, D. et al., *Journal of Chromatography B*, 707:121-1330 (1998).

Klein, E. et al., *Journal of Membrane Science*, 90:69-80 (1994).

Klein, E. et al., *Journal of Membrane Science*, 95:1999-2004 (1994).

Tsuneda, S. et al., *Journal of Chromatography A*, 689:211-218 (1995).

POSITIVELY CHARGED MEMBRANE

CROSS-REFERENCE TO RELATED APPLICATIONS

This application is a continuation of U.S. patent application Ser. No. 11/035,950, filed Jan. 18, 2005 now U.S. Pat. No. 7,094,347, which is a continuation of U.S. patent application Ser. No. 10/891,098, filed Jul. 15, 2004 (issuing as U.S. Pat. No. 6,851,561) which is a continuation of U.S. patent application Ser. No. 09/914,163, filed Dec. 12, 2001 (issuing as U.S. Pat. No. 6,780,327) which is a 371 of PCT/US00/04786, filed on Feb. 25, 2000. This application claims priority from U.S. Provisional Patent Application Nos. 60/121,669 and 60/121,670, both filed on Feb. 25, 1999, the disclosures of which are incorporated herein by reference in their entireties.

TECHNICAL FIELD OF THE INVENTION

The present invention relates to positively charged membranes in general, and, in particular to positively charged membranes comprising a porous substrate. These membranes are useful in detecting, filtering, and/or purifying biomolecules, for example, in ion-exchange chromatography and macromolecular transfer.

BACKGROUND OF THE INVENTION

Detection, filtration, and purification of biomolecules such as proteins, amino acids, nucleic acids, and endotoxins present in fluids such as biological and pharmaceutical fluids have received considerable attention from the industry recently. Ion exchange membranes, particularly positively charged ion exchanged membranes, have been proposed for these purposes. Some of these ion exchange membranes, although they exhibit affinity or binding towards the biomolecules, are not selective. Thus, for example, these membranes have high non-specific protein binding capacity. In addition, the capacities to bind selected proteins of interest are low. Further, preparation of some of the membranes involves complex chemistries or procedures that can lead to increased material and process costs. For example, the preparation can involve radiation grafting of charged monomers, or involve covalently bonding a positive charge modifying polymer to a porous membrane substrate. Further, controlling the chemistry of some of the membranes, e.g., the degree of crosslinking, is rather difficult and/or labor intensive.

Accordingly, there exists a need for a positively charged membrane that has a high binding capacity for biomolecules such as proteins, peptides, amino acids, and nucleic acids. There further exists a need for a positively charged membrane that has low non-specific binding for biomolecules. There further exists a need for a positively charged membrane that involves a relatively simple chemistry, and at the same time permits the degree of crosslinking to be controlled with ease.

These advantages of the present invention, as well as additional inventive features, will be apparent from the description of the invention provided herein.

BRIEF SUMMARY OF THE INVENTION

Figure 1:
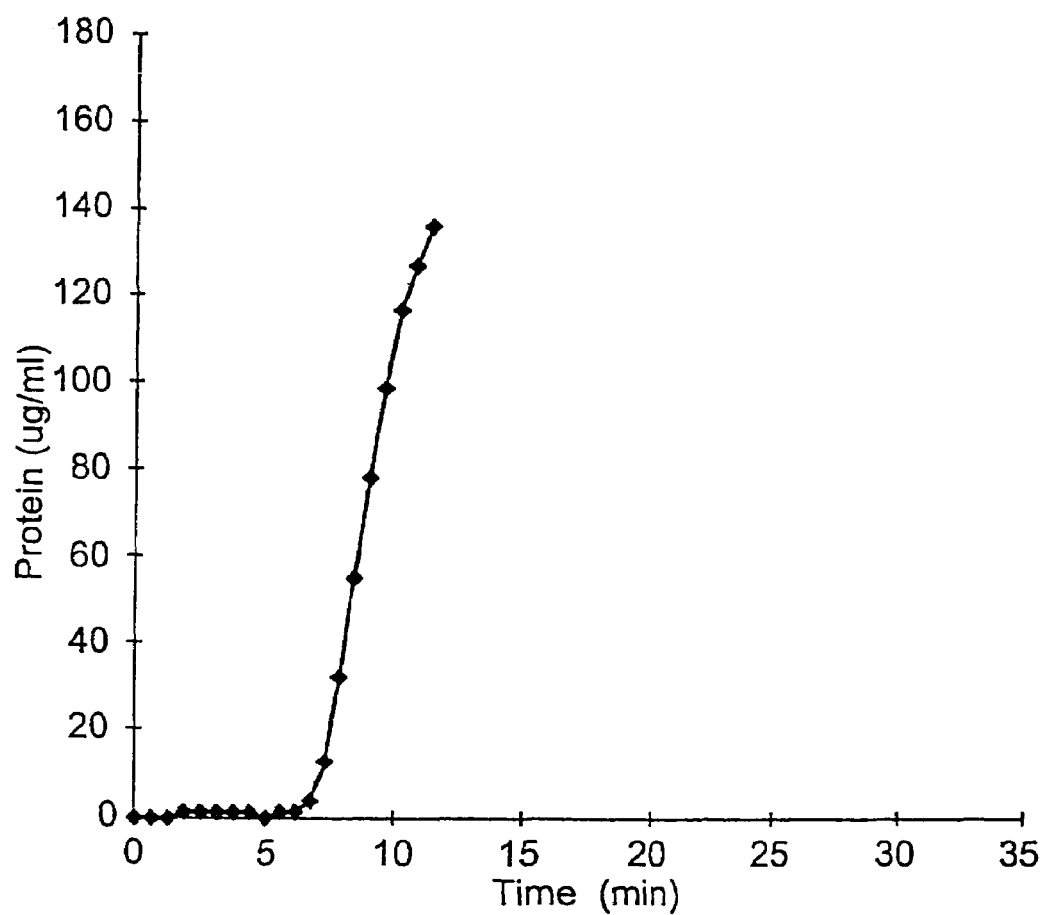
FIG. 1 depicts the breakthrough curve for bovine serum albumin (BSA) obtained on a membrane according to an embodiment of the present invention. The x-axis represents the filtration time, and the y-axis represents the absorbance of the filtrate at 280 nm and is indicative of the concentration of BSA. See Example 1 for additional details.

Many of the foregoing needs have been fulfilled by the present invention which provides a positively charged microporous membrane comprising a porous substrate and a crosslinked coating having pendant cationic groups. In some embodiments, the crosslinked coating comprises a crosslinked polyamine such as a polyalkyleneamine. In a preferred embodiment, the crosslinked coating comprises a polyethyleneimine having pendant cationic groups.

The crosslinked coating can optionally include one or more additional materials which may or may not contain cationic groups. For example, in one embodiment, the crosslinked coating includes a diallylamine copolymer having pendant cationic groups and/or an acrylic copolymer having pendant cationic groups. In preferred embodiments, the porous substrate is hydrophilic. The membranes of the present invention are advantageously free of covalent bonds or grafts with the substrate.

The present invention further provides a positively charged microporous membrane comprising a porous substrate and a coating prepared by crosslinking a composition comprising a diallylamine copolymer having epoxy groups and pendant cationic groups, a polyamine such as a polyalkyleneamine, and an amine reactive compound having a cationic group.

The present invention provides a positively charged microporous membrane having a protein binding capacity (preferably a BSA binding capacity) of about 25 mg/ml or more. The present invention further provides a positively charged microporous membrane comprising a porous polyethersulfone substrate and a crosslinked coating comprising the reaction product of a polyethyleneimine having pendant quaternary ammonium groups and a polyalkyleneglycol polyglycidylether.

The present invention further provides a process for preparing embodiments of the positively charged microporous membranes. In one embodiment, the process comprises contacting with, coating or applying to a porous substrate a composition that can produce a polyamine with pendant cationic groups. For example, in one embodiment, the composition includes a polyalkyleneimine having pendant quaternary ammonium groups and a polyalkyleneglycol polyglycidylether. In an embodiment, the composition can include a diallylamine copolymer having epoxy and pendant cationic groups, a polyalkyleneamine, and an amine reactive compound having a cationic group and curing the substrate. In still another embodiment, the composition comprises a copolymer of diallylamine, a diallyl dialkylammonium halide, and an acrylic monomer having a quaternary ammonium group, and a crosslinking agent. The substrate is cured, for example, by heat. Optionally, the cured substrate can be extracted to remove extractable residues therein.

The present invention further provides devices, e.g., filter devices, chromatographic devices, macromolecular transfer devices and/or membrane modules comprising the membranes of the present invention.

The present invention further provides a process for treating a fluid containing negatively charged particles comprising contacting the fluid with a membrane of the present invention.

The membranes of the present invention find use in various applications such as filtration of fluids containing negatively charged materials such as atoms, molecules, and particulates, and, preferably, biomolecules. The present invention further provides a process for macromolecular transfer from a device or element, e.g., an electrophoresis gel, comprising contacting a membrane of the present invention with the device or element and transferring the macromolecules from the device or element to the membrane.

While the invention has been described and disclosed below in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF EMBODIMENTS

The present invention provides positively charged microporous membranes that find use in a variety of applications including ion-exchange chromatography, filtration, and macromolecular transfer. The membranes of the present invention comprise a porous support and a crosslinked coating having fixed positive charges. In preferred embodiments, the porous support is hydrophilic. The membranes of the present invention have one or more advantageous properties, e.g., high water flow rates, high charge density, and high dynamic protein binding capacity. Some embodiments of the membranes of the present invention have alkali resistance.

In an embodiment, the present invention provides a positively charged microporous membrane having a protein binding capacity, preferably a BSA binding capacity, of about 25 mg/ml or more. The membrane comprises a porous substrate, preferably a hydrophilic porous substrate, and a crosslinked coating having pendant cationic groups.

In some embodiments, the crosslinked coating comprises a crosslinked polyamine such as a polyalkyleneamine. In a preferred embodiment, the crosslinked coating comprises a polyethyleneimine having pendant cationic groups. The crosslinked coating can optionally include other materials such as ingredients, reactants, or polymers, e.g., copolymers. The other ingredients, reactants, or polymers can also include cationic groups, particularly pendant cationic groups. The present invention further includes positively charged membranes having pendant cationic groups that can be produced by interchanging and/or combining the ingredients, reactants, or polymers of the embodiments described herein.

The present invention thus provides, in one embodiment, a positively charged microporous membrane comprising a hydrophilic porous substrate and a crosslinked coating that includes a diallylamine copolymer. The present invention further provides a positively charged microporous membrane comprising a hydrophilic porous substrate and a crosslinked coating that includes an acrylic copolymer. The cationic groups are preferably linked to backbone of the crosslinked coating, particularly to the copolymer backbone, through spacer groups.

The present invention provides, in embodiments, a positively charged microporous membrane comprising a hydrophilic porous substrate and a coating prepared by crosslinking a composition comprising a diallylamine copolymer having epoxy groups and pendant cationic groups, a polyamine such as a polyalkyleneamine, and an amine reactive compound having a cationic group. In some embodiments, the present invention further provides a positively charged microporous membrane comprising a hydrophilic porous substrate and a coating prepared by crosslinking a composition comprising diallylamine, a diallyldialkylammonium halide, an acrylic monomer having a quaternary ammonium group, and a crosslinking agent.

In a preferred embodiment, the present invention further provides a microporous membrane comprising a porous support and a crosslinked polyamine coating, particularly a crosslinked polyalkyleneamine coating, that provides a fixed positive charge. The present invention further provides a positively charged microporous membrane comprising a hydrophilic porous polyethersulfone substrate and a crosslinked coating comprising the reaction product of a polyethyleneimine having pendant quaternary ammonium groups and a polyalkyleneglycol polyglycidylether. The present invention provides a positively charged microporous membrane comprising a hydrophilic porous substrate and a crosslinked coating comprising a polyamine, such as a polyalkyleneamine, having pendant cationic groups.

The pendant cationic group of the membrane can be any suitable cationic group—ammonium, sulfonium, phosphonium, or other group, preferably an ammonium group. An example of a preferred ammonium group is a quaternary ammonium group such as a tetraalkylammonium group. It has been found that the cationic groups when present as pendant groups, rather than as part of the backbone, provide enhanced biomolecule or charged material binding capacity and/or selectivity.

The cationic groups can be linked to the backbone directly through a bond such as a mono or divalent covalent bond, and preferably, the cationic groups are linked and spaced away from the backbone of the coating. Spacer groups can be included between the backbone and the cationic groups to provide spatial charge separation and an increased opportunity for the fixed charges to interact with charged materials being treated such as proteins, amino acids, and nucleic acids. The spacer group provides enhanced biomolecule binding capacity and/or selectivity.

Any suitable spacer group can be employed, preferably a polar group such as a spacer group that includes a polar moiety. Thus, for example, the spacer group includes one or more moieties selected from the group consisting of hydroxy, hydroxyalkyl, amino, imino, aminoalkyl, amido, alkylamido, urea, urethane, ester, and alkoxyalkyl.

In certain embodiments, the spacer group includes one or more moieties selected from the group consisting of hydroxyalkyl, alkylamino, hydroxyalkylaminoalkyl, hydroxyalkylaminoalkyl hydroxyalkyl, alkylaminoalkyl, and alkylamido. In certain other embodiments, the spacer group includes one or more moieties selected from the group consisting of hydroxyalkyl, alkylamino, hydroxyalkylaminoalkyl, hydroxyalkylaminoalkyl hydroxyalkyl, alkylaminoalkyl, and alkylamido.

The spacer group can be linear, branched, or combinations thereof. The cationic groups can become integral parts of the coating as a result of attachment of the cationic groups with the aid of reactants that link the cationic groups to the backbone of the coating through spacer groups. In certain embodiments, the cationic groups can be attached to precursors through spacer groups and the precursors can be converted to or become part of the coating chemistry.

The spacer group can of any suitable length, for example, the spacer group can be a group having from 1 to about 10 atoms, e.g., carbon atoms. Thus, the spacer group can be from 1 to about 10 carbon atoms long, preferably from 2 to about 6 carbon atoms long, and more preferably about 3 carbon atoms long. Without intending to be bound to any particular mechanism, the spacer group, which helps provide spatial separation among the cationic groups, is believed to have a role in enhancing the interaction between the biomolecule and the membrane and in the binding capacity that is manifested as a result of that interaction.

A preferred spacer group is hydroxyalkyl. Thus, e.g., the polyamine can be contacted with a glycidyl compound having a cationic group so that the epoxy ring opens at the primary or secondary amino groups of the polyalkyleneamine. Further, a solution of a polyamine such as polyethyleneimine (PEI) can be combined with, e.g., glycidyl trimethylammonium chloride, and the polyamine having trimethylammonium chloride pendant groups linked through hydroxyalkyl groups can be obtained.

The quantities of the reactants for the linking reaction are chosen so that the resulting polyamine having pendant cationic groups contains reactive sites for crosslinking. Thus, for example, the polyamine contains residual primary and/or secondary amino groups after the linking reaction has been carried out. Accordingly, it is preferred that the residual primary and/or secondary amino groups are at least about 10%, and more preferably from about 10% to about 40%, by mole, of the primary and/or secondary amino groups on the polyamine prior to linking of the pendant cationic groups.

The embodiment membrane that includes a coating comprising a diallylamine copolymer can be further described as follows. The copolymer comprises polymerized diallylamine monomer. The diallylamine monomer can be substituted or unsubstituted. Thus, for example, an alkyl substituted diallylamine such as diallylmethylamine can be used. Preferably, the diallylamine copolymer further includes an acrylic monomer. The acrylic monomer preferably contains the cationic group. The acrylic monomer could be an acrylate ester or an acrylamide. The term "acrylic" herein includes unsubstituted as well as substituted acrylic monomers. An example of a substituted acrylic monomer is an alkylacrylic monomer.

The term "alkyl" herein refers to an alkyl group having 1 to about 10 carbon atoms, preferably from 1 to about 6 carbon atoms.

An example of a suitable acrylamide monomer is an acryloylaminoalkyl monomer. An example of the acryloylaminoalkyl monomer is methacryloylaminopropyl trimethylammonium chloride. An example of an acrylate is an acryloyloxyalkyl monomer.

In certain embodiments of the present invention, the diallylamine copolymer includes one or more comonomers. These comonomers are preferably nitrogen containing monomers. These comonomers preferably contain tertiary and/or quaternary ammonium groups. Examples of preferred comonomers include diallyldialkylammonium chloride and dialkylaminoalkyl acrylamide. Thus, in certain embodiments, the diallylamine copolymer includes in addition to diallylamine, comonomers such as methacryloylaminopropyl trimethylammonium chloride, diallyldimethylammonium chloride, and dimethylaminopropyl methacrylamide. The acrylic copolymer can also include an acrylate monomer in place of, or in addition to, the acrylamide monomer.

The diallylamine copolymer can be prepared by methods known to those of ordinary skill in the art. For example, diallylamine and monomers carrying cationic and epoxy groups can be polymerized to provide a suitable diallylamine copolymer.

Alternatively, a diallylamine copolymer that contains cationic groups can be prepared first, and then, the epoxy groups can be introduced. Thus, e.g., the copolymer can be reacted an reactive epoxy group containing compound, e.g., epichlorohydrin.

A mixture of diallylamine and the acrylic monomer is allowed to polymerize under suitable conditions. For example, a free radical initiator such as ammonium persulfate can be employed to initiate the polymerization. The molar ratio between diallylamine and the acrylic monomer can be from about 0.05 to about 4, preferably from about 0.1 to about 2, and more preferably from about 0.5 to about 1.

The diallylamine copolymer is then reacted with epichlorohydrin. The chloromethyl group of epichlorohydrin reacts with the secondary or primary amino groups of the copolymer to provide a polymer having pendant epoxy groups. The degree of substitution of epoxy groups can be from about 10% to about 200%, preferably from about 25% to about 175%, and more preferably from about 50% to about 150%, by mole of the diallylamine in the copolymer.

Some of the cationic groups of the coating can become part of the coating chemistry by attaching them through amino spacer groups. Amino spacer groups can be provided by the use of one or more polyamines such as polyalkyleneamines. Examples of polyalkyleneamines include short chain polyalkyleneamines such as diethylenetriamine, triethylenetetramine, tertaethylenepentamine, and pentaethylenehexamine, and the like, and long chain polyalkylenamines, such as polyethyleneimine (PEI). The polyamines have a molecular weight of greater than about 500. Any suitable polyamine amine can be used. Preferably a PEI is used. Any suitable PEI can be used. The molecular weight of the PEI can be from about 500 to about 750,000, preferably from about 10,000 to about 750,000, and more preferably from about 50,000 to about 100,000. In certain embodiments of the present invention, a combination of a short chain polyalkyleneamine and a long chain polyalkyleneamine can be used advantageously.

The cationic groups can be attached to the polyalkyleneamine through suitable spacer groups. For example, the polyalkyleneamine can be reacted with a glycidyl compound bearing a cationic group, e.g., glycidyl trialkylammonium halide, to provide a polyalkyleneamine having cationic groups linked to the polyalkyleneamine through hydroxyalkyl spacer groups. Thus, for example, pentaethylenehexamine can be reacted with glycidyl trimethylammonium chloride.

The polyalkyleneamine that is modified to have cationic groups as described above can be made part of the coating chemistry by reacting it with the diallylamine copolymer having suitable reactive sites, e.g., epoxy groups. The diallylamine copolymers can be made to possess reactive sites by reacting with compounds that provide reactive sites. Thus, for example, the diallylamine copolymer can be reacted with epichlorohydrin to provide epoxy sites. The coating is crosslinked as a result of reaction among the reactive sites such as epoxy and amine groups. In some embodiments of the present invention, the coating further includes a crosslinking agent. Any suitable crosslinking agent can be used. The crosslinking agent is preferably a polyglycidyl compound, for example, a polyalkyleneglycol polyglycidylether. A preferred example of a crosslinking agent is ethylene glycol diglycidyl ether.

The present invention further provides a positively charged microporous membrane comprising a hydrophilic porous substrate and a crosslinked coating, particularly a crosslinked polyalkyleneamine coating, that provides a fixed positive charge. The present invention further provides a positively charged microporous membrane comprising a hydrophilic porous polyethersulfone substrate and a crosslinked coating comprising the reaction product of a polyethyleneimine having pendant quaternary ammonium groups and a polyalkyleneglycol polyglycidylether.

For example, the coating can be created by coating and curing a hydrophilic substrate with a composition comprising, in suitable amounts, a diallylamine copolymer, a polyamine such as a polyalkyleneamine, and an amine reactive agent having a cationic group, such as glycidyl trimethylammonium chloride. For example, the diallylamine copolymer can be present in an amount of from about 1% to about 20%, preferably in an amount of from about 2% to about 10%, and more preferably in an amount of from about 3% to about 7% by weight of the composition. The polyamine can be present in an amount of from about 0.05% to about 5%, preferably in an amount of from about 0.1% to about 2%, and more preferably in an amount of from about 0.2% to about 1% by weight of the composition. The ratio of amine reactive cationic compound and active hydrogen of polyalkyleneamine can be present in an amount of from about 0.1% to about 20%, preferably in an amount of from about 0.5% to about 15%, and more preferably in an amount of from about 0.75% to about 10% by weight of the composition.

Certain embodiments of a membrane according to the present invention can be prepared by coating and curing a hydrophilic substrate with a coating composition comprising diallylamine, diallyldimethylammonium halide, an acrylic monomer, and a crosslinking agent. An example of a suitable diallyldialkylammonium halide is diallyldimethylammonium chloride. Any suitable crosslinking agent can be used. A preferred crosslinking agent is an N-(alkoxymethyl)-acrylamide. The crosslinking acrylamide can be further substituted. For example, an alkylacrylamide having N-(alkoxymethyl) group can be used. Preferred crosslinking agents are N-(isobutoxymethyl)acrylamide and N-(isobutoxymethyl)methacrylamide. The ingredients of the composition can be in any suitable proportion.

For example, the acrylic monomer can be present in an amount of from about 0.1% to about 30%, preferably in an amount of from about 1% to about 20%, and more preferably in an amount of from about 1% to about 15% by weight of the composition. The diallylamine can be present in an amount of from about 0.1% to about 30%, preferably in an amount of from about 1% to about 20%, and more preferably in an amount of from about 1% to about 15% by weight of the composition. The diallylamine dialkylammonium halide can be present in an amount of from about 0.1% to about 30%, preferably in an amount of from about 1% to about 20%, and more preferably in an amount of from about 2% to about 15% by weight of the composition. The crosslinking agent can be present in an amount of from about 0.1% to about 20%, preferably in an amount of from about 1% to about 15%, and more preferably in an amount of from about 2% to about 10% by weight of the composition.

In certain embodiments of the present invention, the crosslinked coating comprises an acrylic copolymer having pendant cationic groups linked to the copolymer through spacer groups. Any of the spacer groups described above can be utilized. An example of the acrylic monomer is alkylacryloylaminoalkyl trialkylammonium halide, preferably methacryloylaminopropyl trimethylammonium chloride. Thus, the coating composition includes an acrylic copolymer that has epoxy groups and pendant cationic groups. The acrylic copolymer comprises a glycidylalkylacrylate and a methacryloyloxyalkyl or methacryloylaminoalkyl trialkylammonium halide, and preferably glycidyl methacrylate and methacryloyloxyethyl or methacryloylaminopropyl trimethylammonium chloride. It is further preferred that the acrylic copolymer in its crosslinked state includes a polyamine. A short chain polyalkyleneamine is a further preferred polyamine.

Thus, e.g., the acrylic copolymer in its crosslinked state includes pentaethylenehexamine. Preferably, the polyamine is a modified polyamine. Thus, the polyamine is modified by a compound having cationic groups. The polyamine is modified by glycidyl trimethylammonium chloride. The coating composition can include the ingredients in any suitable proportion. For example, the acrylic polymer can be present in an amount of from about 0.5% to about 5%, preferably in an amount of from about 1% to about 4.5%, and more preferably in an amount of from about 1.25% to about 4.25% by weight of the composition. The polyamine can be present in an amount of from about 0.5% to about 10%, preferably in an amount of from about 1% to about 8%, and more preferably in an amount of from about 3% to about 6% by weight of the composition.

The polyamine having pendant cationic groups can be crosslinked by any suitable crosslinking agent. The crosslinking agent is a polyfunctional agent having amine reactive groups such as epoxy, isocyanato, carboxyl, and acid chloride. A preferred crosslinking agent is a polyglycidyl compound. An example of a suitable polyglycidyl compound is a polyalkyleneglycol polyglycidylether. Ethyleneglycol diglycidyl ether and butyleneglycol diglycidyl ether are preferred crosslinking agents.

The coating composition can be prepared, e.g., by dissolving the polyamine in a suitable solvent. Preferred solvents include water, low boiling alcohols such as methanol, ethanol, and propanol, and combinations thereof. The solvent can be present in an amount of from about 40% to about 99%, and preferably in an amount of from about 90% to about 99% by weight of the coating composition. The polyamine can be present in an amount of from about 1% to about 5%, and preferably in an amount of from about 1% to about 2.5% by weight of the coating composition.

The positively charged microporous membrane can be made by coating a porous substrate, preferably a porous hydrophilic substrate, and curing the coated substrate. The hydrophilic porous substrate can be made of any suitable material; preferably, the substrate comprises a polymer. Examples of suitable polymers include polyaromatics, polysulfones, polyamides, polyimides, polyolefins, polystyrenes, polycarbonates, cellulosic polymers such as cellulose acetates and cellulose nitrates, fluoropolymers, and PEEK. Aromatic polysulfones are preferred. Examples of aromatic polysulfones include polyethersulfone, bisphenol A polysulfone, and polyphenylsulfone. Polyethersulfone is particularly preferred. The hydrophilic porous substrate can have any suitable pore size, for example, a pore size of from about 0.01 or 0.03 μm to about 10 μm, preferably from about 0.1 μm to about 5 μm, and more preferably from about 0.2 μm to about 5 μm. The porous substrate can be asymmetric or, in a preferred embodiment, symmetric.

The porous substrate can be prepared by methods known to those of ordinary skill in the art. For example, the porous substrate can be prepared by a phase inversion process. Thus, a casting solution containing the polymer, a solvent, a pore former, a wetting agent, and optionally a small quantity of a non-solvent is prepared by combining and mixing the ingredients, preferably at an elevated temperature. The resulting solution is filtered to remove any impurities. The casting solution is cast or extruded in the form of a sheet or hollow fiber. The resulting sheet or fiber is allowed to set or gel as a phase inverted membrane. The set membrane is then leached to remove the solvent and other soluble ingredients.

The porous substrate can be coated with the coating solution by methods known to those of ordinary skill in the art, for example, by dip coating, spray coating, meniscus coating, and the like. Dip coating, for example, can be carried out as follows. The substrate is immersed in the solution for a given period of time sufficient to insure coating of the pore walls. The immersion time can be from about 1 second to about 5.0 minutes, preferably from about 1 second to about 1.0 minutes, and more preferably from about 0.1 minute to about 0.3 minute. Following the immersion, the excess coating solution on the substrate is removed by allowing it to drain under gravity or by the use of a squeegee or air knife. The resulting coated substrate is cured to effect the curing or crosslinking of the coating composition. Thus, for example, the membrane can be cured at a temperature of below 130° C., e.g., from about 50° C. to about 130° C., and preferably at a temperature of from about 70° C. to about 130° C., for a suitable period of time, which can range from about 5 minutes to about 60 minutes, and preferably from about 10 minutes to about 30 minutes. The resulting membrane can be washed to leach out any extractable in the membrane. Illustratively, the membrane can be leached in hot deionized water, e.g., in water held above 73° C. The resulting membrane is then dried in air or in an oven to remove the water.

The present invention provides a process for preparing a positively charged microporous membrane comprising a crosslinked polyamine having pendant cationic groups. In an embodiment, the process comprises:

(a) providing a porous substrate;
(b) contacting the substrate with a composition comprising a crosslinking agent and a polyamine having pendant cationic groups;
(c) curing the substrate obtained in (b) to obtain the positively charged membrane; and
(d) optionally, extracting the membrane obtained in (c) to remove extractable residue therein.

The present invention further provides a process for preparing certain embodiments of the positively charged microporous membrane comprising a diallylamine copolymer having pendant cationic groups. An embodiment of the process comprises:

(a) providing a porous substrate;
(b) contacting the substrate with a composition comprising a diallylamine copolymer having epoxy and pendant cationic groups, a polyamine, and an amine reactive compound having a cationic group;
(c) curing the substrate obtained in (b) to obtain the positively charged membrane; and
(d) optionally, extracting the membrane obtained in (c) to remove extractable residue therein.

The present invention further provides a process for preparing another embodiment of the present invention, e.g., a microporous membrane comprising a diallylamine copolymer having pendant cationic groups, an embodiment of the process comprising:

(a) providing a hydrophilic porous substrate;
(b) contacting the substrate with a composition comprising a copolymer of a diallylamine, diallyldialkylammonium halide, an acrylic monomer having a quaternary ammonium group, and a crosslinking agent;
(c) curing the substrate obtained in (b) to obtain the positively charged membrane; and
(d) optionally, extracting the membrane obtained in (c) to remove extractable residue therein.

The present invention thus provides a process for preparing an embodiment of the positively charged microporous membrane comprising an acrylic copolymer having epoxy groups and pendant cationic groups, an embodiment of the process comprising:

(a) providing a porous substrate;
(b) contacting the substrate with a coating composition comprising an acrylic copolymer having epoxy groups and pendant cationic groups;
(c) curing the substrate obtained in (b) to obtain the positively charged membrane; and
(d) optionally, extracting the membrane obtained in (c) to remove extractable residue therein.

The present invention further provides a positively charged microporous membrane comprising a hydrophilic porous polyethersulfone substrate and a crosslinked coating comprising the reaction product of a polyethyleneimine having pendant quaternary ammonium groups and a polyalkyleneglycol polyglycidylether.

The present invention further provides a positively charged microporous membrane comprising a hydrophilic porous substrate and a crosslinked coating comprising a polyalkyleneamine having pendant cationic groups linked to the polyalkyleneamine through spacer groups.

The present invention further provides a positively charged microporous membrane comprising a hydrophilic porous polyethersulfone substrate and a crosslinked coating comprising the reaction product of a polyethyleneimine having pendant quaternary ammonium groups and a polyalkyleneglycol polyglycidylether.

The present invention further provides a positively charged microporous membrane comprising a hydrophilic porous substrate and a crosslinked coating comprising a diallylamine copolymer having pendant cationic groups linked to the diallylamine copolymer through spacer groups.

The present invention further provides a positively charged microporous membrane comprising a hydrophilic porous substrate and a crosslinked coating comprising an acrylic copolymer having pendant cationic groups linked to the acrylic copolymer through spacer groups.

The present invention further provides a positively charged microporous membrane comprising a hydrophilic porous substrate and a crosslinked coating, wherein the coating is prepared by crosslinking a composition comprising a diallylamine copolymer having epoxy groups and pendant cationic groups, a polyalkyleneamine, and an amine reactive compound having a cationic group.

The present invention further provides a positively charged microporous membrane comprising a hydrophilic porous substrate and a crosslinked coating composition comprising a copolymer of diallylamine, diallyldialkylammonium halide, acrylic monomer having a quaternary ammonium group, and a crosslinking agent.

The present invention further provides a positively charged microporous membrane comprising a hydrophilic porous substrate and a crosslinked coating composition comprising an acrylic polymer having epoxy groups and pendant cationic groups and a copolymer comprising a polyamine and a glycidyl compound having a cationic group.

The present invention further provides a device, e.g., a filter device, chromatography device, macromolecular transfer device, flow distributor arrangement, and/or a membrane module comprising the positively charged membrane of the present invention. The device can be in any suitable form. For example, the device can include a filter element comprising the positively charged membrane sheet, e.g., in a substantially planar or pleated form. In an embodiment, the element can have a hollow generally cylindrical form. If desired, the device can include the filter element in combination with upstream and/or downstream support or drainage layers. The device can include a plurality of membranes, e.g., to provide a multilayered filter element, or stacked to provide a membrane module, such as a membrane module for use in membrane chromatography. Filter cartridges can be constructed by including a housing and endcaps to provide fluid seal as well as at least one inlet and at least one outlet. The devices can be constructed to operate in cross-flow or tangential flow modes as well as dead-end modes. Accordingly, the fluid to be treated can be passed, for example, tangentially to the membrane surface, or passed perpendicular to the membrane surface. For embodiments of the membrane which are in the form of a tube or fiber, or bundles of tubes or fibers, the membrane(s) can be configured as modules, e.g., after potting their ends in an adhesive. For a description of illustrative chromatographic devices, porous medium modules, and flow distributor arrangements, see U.S. Provisional Patent Application Nos. 60/121,667 and 60/121,701, both filed on Feb. 25, 1999; U.S. Provisional Patent Application Nos. 60/168,738 and 60/168,750, both filed on Dec. 6, 1999; and International Applications filed on Feb. 25, 2000 and entitled "Negatively Charged Membrane" by Chung-Jen Hou, Peter Konstantin, and Yujing Yang; "Chromatography Devices and Flow Distributor Arrangements Used in Chromatography Devices" by Mark Hurwitz, Thomas Sorensen, John Stempel, and Thomas Fendya; and "Chromatography Devices, Porous Medium Modules Used in Chromatography Devices and Methods for Making Porous Medium Modules" by Mark Hurwitz, Thomas Fendya, and Gary Bush. See also UK Patent Application GB2 275 626 A.

The membrane of the present invention, in preferred embodiments, has excellent water permeability, protein binding capacity, and charge density. Thus, for example, the membrane has a water flow rate of at least 5 mL/minute/cm$^2$, e.g., from about 10 mL/minute/cm$^2$ to about 100 mL/minute/cm$^2$, and preferably from about 30 mL/minute/cm$^2$ to about 70 mL/minute/cm$^2$, at 24 inches Hg pressure. The membrane of the present invention has an open water bubble point of below 45 psi, e.g., from about 15 psi to about 35 psi, and preferably from about 20 psi to about 30 psi. The membrane of the present invention is preferably instantly wettable by water and saline solutions.

The membrane of the present invention has high charge density. The charge density can be determined by methods known to those of ordinary skill in the art. For example, a negatively charged dye binding capacity can be used as a measure of the charge. Thus, the membrane has a Metanil Yellow Dye binding capacity of at least 70 mL, e.g., from about 70 mL to about 1000 mL, and preferably from about 90 mL to about 800 mL, when tested with a 10 ppm dye solution in water. Metanil Yellow is a negatively charged dye. The dye binding capacity can be measured by, for example, filtering under a 5 inch Hg negative pressure, a 10 ppm by weight solution, pH 6.6, of Metanil Yellow Dye in a membrane disc of 9.6 square centimeters, and monitoring the volume of the filtrate until a trace of the dye begins to appear in the filtrate.

The membrane of the present invention has high protein binding capacity, preferably a high BSA dynamic binding capacity. Thus, the membrane has a BSA dynamic binding capacity of at least 20 mg/mL, e.g., from about 20 mg/mL to about 100 mg/mL and preferably from about 25 mg/mL to about 80 mg/mL. Illustratively, the BSA dynamic binding capacity is determined by the following method. A fluid containing a protein such as a low ion strength fluid, e.g., 25 mM Tris or 10 mM phosphate containing a protein is passed through a membrane, typically at a flow rate of 1 cm/min, and the concentration of the protein in the filtrate is measured as a function of time. The concentration of the protein can be determined spectrophotometrically, e.g., by measuring the absorbance of the protein at 280 nm. A breakthrough curve such as the one shown in FIG. 1 can then be constructed with the x-axis depicting the time of the filtration experiment and the y-axis depicting the protein concentration in the filtrate.

The membranes of the present invention, particularly those containing a crosslinked coating of the diallylamine copolymer have enhanced stability in alkali relative to membranes comprising a coating composition composed of esters such as glycidyl methacrylate. Thus, the membrane remained stable after soaking in 1M NaOH solution at 37° C. for 48 hours. This alkali resistance allows periodic cleaning and rejuvenation of the spent membrane with an alkali solution.

The membranes of the present invention find use in various applications such as filtration of fluids containing negatively charged materials, e.g., atoms, molecules, and particulates, chromatographic separation, and macromolecular transfer of nucleic acids, and proteins from electrophoresis gels to an immobilizing matrix. Other applications include, for example, purification of viral vaccines and gene therapy vectors. Examples of a negatively charged materials include biomolecules such as proteins, e.g., host cell proteins, peptides, amino acids, nucleic acids such as DNA and RNA, endotoxins, viruses, adenoviruses, and lipids. The membranes of the present invention also find use in the removal of bacterial fragments such as endotoxins from fluids. Examples of nucleic acids include modified or unmodified, natural or synthetic, RNA and DNA. The membrane of the present invention can also be employed to adsorb and/or separate plasmids and/or adenoviruses.

Accordingly, the present invention provides a process for treating a fluid containing negatively charged materials, the process comprising placing the fluid in contact with the positively charged membrane. The present invention further provides a process for selectively adsorbing one or more negatively charged materials from a fluid containing a mixture of negatively charged materials comprising contacting the fluid with the membrane under conditions favorable to the adsorption of selected negatively charged materials. The present invention further provides a process for selectively releasing one or more biomolecules from a membrane of the present invention comprising contacting the membrane having adsorbed biomolecules with an eluant under conditions favorable to the release of the selected biomolecules.

The positively charged membrane of the present invention is particularly suitable for treating fluids containing biomolecules that already have or that are treated to have a negative surface charge. For example, a protein solution can be treated so that the pH of the solution is higher than the isoelectric point of the protein, preferably up to about 3 or 4 units higher than the isoelectric point. Thus, e.g., BSA has an isoelectric point of 4.7. The pH of the buffer containing the protein can be adjusted to about 7.0. BSA, which has a negative charge, can be adsorbed to the surface of the positively charged membrane.

The membrane of the present invention can be employed in the purification of proteins. Thus, e.g., nucleic acids can be removed from a fluid comprising nucleic acids and proteins. An example of a protein is antibody. The nucleic acids can be, for example, genomic DNA, plasmid DNA, or viral DNA. The nucleic acid can be removed with minimal loss of protein. The membrane of the present invention has DNA binding capacity of about 5 mg/ml or more at about 80% saturation or more. Embodiments of the membrane have a DNA binding capacity of 5.7 mg/ml at a flow rate of 20 ml/min and 8.5 mg/ml at a flow rate of 4 ml/min. In some embodiments of the processes, for example, wherein nucleic acids such as DNA are to be removed from a fluid, e.g., a pharmaceutical preparation containing nucleic acid and protein, the DNA (e.g., host cell DNA) can be reduced from an initial concentration of about 100 µg/ml or more down to about 10 picogram/ml or less in the processed (e.g., filtered) nucleic acid-depleted protein-containing fluid. DNA binds to the membrane of the present invention even in highly saline media such as 0.5 M NaCl at pH 7.0.

The membranes of the present invention also can be used in the separation of proteins, e.g., in the isolation or purification of the individual proteins from a fluid containing IgG and BSA. The separation can be effected by varying the process conditions, e.g., the pH or the buffer or both. For example, 80 µl of a fluid containing 1 mg/ml goat IgG and 1 mg/ml BSA can be placed on a chromatographic column or stack of 5 layers of a 25 mm diameter positively charged membrane of the present invention. The column or stack can be eluted under a gradient—7 ml from 25 mM Tris buffer at a pH of 8.5 to 1M NaCl-25 mM Tris buffer at a pH of 8.5. The flow rate can be 4 ml/min. The goat IgG elutes first, followed by BSA.

The membrane of the present invention has a dynamic protein binding capacity of about 25 mg/ml or higher at 80% saturation capacity, e.g., in a 25 mM Tris buffer pH 7.0 at a 1 ml/minute flow rate. Embodiments of the membrane have dynamic protein, e.g., BSA, binding capacity of 80 mg/ml in a 0.5 M salt solution.

The following examples further illustrate the present invention, but of course should not be construed in any way as limiting the scope of the invention.

EXAMPLE 1

This Example illustrates a method of preparing an embodiment of the positively charged membrane of the present invention. This Example further illustrates the properties of the prepared membrane. A diallylamine copolymer was prepared first as follows. 5 grams of diallylamine were added to 59 grams of deionized water containing 12 grams of 50% hydrochloric acid solution. 30 grams of {3-(methacryloylamino)propyl}-trimethylammonium chloride (50% solution) were added and mixed. The pH of the resulting solution was adjusted to 5.0 by the addition of dilute sodium hydroxide. The above reaction mixture was purged with nitrogen for 2 hours at 50° C.

Polymerization was initiated by the addition of 0.5 gram of ammonium persulfate. The polymerization was stopped after 2.5 hours. The resulting polymer solution was activated by reaction with epichlorohydrin. 20 grams of the above prepared copolymer solution were diluted with an equal amount of deionized water. The pH of the diluted solution was adjusted to 8.0 by the addition of dilute NaOH, and 1.3 grams of epichlorohydrin were added. The mixture obtained was stirred vigorously at 45° C. for 4 hours. An activated polymer solution was thus obtained.

Separate from the above prepared activated polymer solution, 10 grams of pentaethylenehexamine (PEHA) (Aldrich) and 56 grams of glycidyl trimethylammonium chloride (GTMACI) (90%) (Fluka) were dissolved in 34 grams of deionized water, and the resulting solution was heated in a water bath at 135° F. overnight. A crosslinker solution was thus obtained.

Two different membrane coating solutions were prepared. The first solution contained 20 grams of the activated polymer, 20 grams of deionized water, 3 grams of the crosslinker solution. The second solution contained 20 grams of the activated polymer and 4 grams of the crosslinker solution. The pH of the solutions was adjusted to 10.4 by the addition of NaOH.

Microporous polyethersulfone membranes were used as the hydrophilic substrate. The solutions were coated on a hydrophilic polyethersulfone membrane of nominal pore size of 0.8 µm. Two pieces of the membrane substrate were soaked in the coating solutions. The excess solution was removed, and the soaked substrates were heated in an oven at 100° C. for 1 hour. The resulting membranes were extracted in hot deionized water for 1 hour, and then dried. The membrane produced from the first coating solution (Membrane 1A) had a water flow rate of 50.8 ml/min/cm$^2$ at 10 psi, a Metanil Yellow Dye binding capacity of 270 ml, and a BSA binding capacity of 17.81 mg/ml. The membrane produced from the second coating solution (Membrane 1B) had a water flow rate of 12.0 ml/min/cm$^2$ at 10 psi, and a BSA binding capacity of 49.99 mg/ml. The breakthrough curve obtained for membrane 1B is set forth in FIG. 1.

EXAMPLE 2

This Example illustrates a method of preparing another embodiment of the positively charged membrane of the present invention. This Example further illustrates the properties of the prepared membrane. A diallylamine copolymer was prepared as follows.

A mixture containing 680 grams of water, 30 grams of concentrated hydrochloric acid, 30 grams of diallylamine, 46.2 grams of a 65% solution of diallyldimethylammonium chloride, 30 grams of N-{3-(dimethylamino)propyl}-methacrylamide, and 180 grams of a 50% solution of 3-{methacryloylamino)propyl}-trimethylammonium chloride was prepared. The pH of the mixture was adjusted to 4.5, the solution was degassed, and polymerization was carried out. 3 grams of ammonium persulfate and 1.2 grams of sodium metabisulfite were added to initiate the polymerization. After the polymerization was completed, the pH of the polymer solution was further adjusted to 10.5, and 42.7 grams of epichlorohydrin was added to the solution. The resulting solution was held at a temperature of 45–60° C. for several hours. The polymer solution was then cooled to the ambient temperature.

241.8 grams of the polymer solution prepared as above, 460 grams of water, 13.6 grams of PEHA, and 10 grams of GTMACI were combined and mixed to obtain a coating solution. A hydrophilic polyethersulfone having a nominal pore size of 0.8 µm was coated with the coating solution, and the coated membrane was cured in an oven at about 100° C.

for 1 hour. The cured membrane was then washed in hot deionized water and dried. The protein binding capacity membranes thus prepared was determined to be in the range of 40–62 mg of BSA/ml.

EXAMPLE 3

This Example illustrates a method of preparing yet another embodiment of the positively charged membrane of the present invention. This Example further illustrates the properties of the prepared membrane. A diallylamine copolymer was prepared as follows.

711 grams of deionized water, 30 grams of concentrated hydrochloric acid, 30 grams of diallylamine, 46.2 grams of a 65% solution of diallyldimethylammonium chloride, and 180 grams of a 50% solution of 3-{methacryloylamino)propyl}-trimethylammonium chloride were mixed, and the pH of the mixture was adjusted to 4.5 by the addition of hydrochloric acid (36%). The resulting solution was degassed, and polymerization was carried out using the combination of ammonium persulfate and sodium metabisulfite as the initiator. The pH of the resulting polymer solution was adjusted to 10.5, and 27.0 grams of epichlorohydrin were added. The mixture obtained was kept at a temperature of 45–60° C. for several days, and then cooled to the ambient temperature.

300.0 grams of the polymer solution prepared as above, 300.0 grams of deionized water, 5.0 grams of PEHA, 5.0 grams of PEI of molecular weight (Mn approximately 600) from Aldrich (water free), 6.0 grams of GTMACl, and 5.0 grams of ethylene glycol diglycidyl ether were combined and mixed to obtain a coating solution. A hydrophilic polyethersulfone having a nominal pore size of 0.8 μm and including a crosslinked hydrophilic wetting agent was coated with the coating solution, and the coated membrane was cured in an oven at about 100° C. for 1 hour. The cured membrane was then washed in hot deionized water and dried. The protein (BSA) binding capacity of the membranes thus prepared was determined to be in the range of 36–45 mg/ml. The coating solution also was used to modify a SUPOR™ EK polyethersulfone membrane. The resulting membrane had a BSA binding capacity of 41 mg/ml.

EXAMPLE 4

This Example illustrates a method of preparing still another embodiment of the positively charged membrane of the present invention. This Example further illustrates the properties of the prepared membrane. A diallylamine copolymer was prepared as follows.

575 grams of water, 100 grams of methanol, 30 grams of concentrated hydrochloric acid, 30 grams of diallylamine, 46.2 grams of 65% solution of diallyldimethylammonium chloride, 30 grams of N-(isobutoxymethyl)acrylamide, and 180 grams of 50% of {3-(methacryloylamino)propyl}-trimethylammonium chloride were combined, and the pH of the resulting solution was adjusted to 4.5 by the addition of concentrated hydrochloric acid (36%). The solution was then degassed and polymerized using the combination of ammonium persulfate and sodium metabisulfite as the initiator. The polymer solution prepared as above was diluted with water (1:4 by weight) to obtain a coating solution.

A polyethersulfone substrate of approximate pore size 0.65 μm was coated with the coating solution, and the coated membrane was cured in an oven at about 100° C. for 1 hour. The cured membrane was then washed in hot deionized water and dried. The protein (BSA) binding capacity of the membrane thus prepared was found to be 24 mg/ml.

EXAMPLE 5

This Example illustrates a method of preparing still another embodiment of the positively charged membrane of the present invention. This Example further illustrates the properties of the prepared membrane. An acrylic polymer having epoxy groups and pendant cationic groups was prepared as follows.

30 grams of glycidyl methacrylate (Aldrich), 200 grams dimethylformamide, 949 grams of deionized water, and 266 grams of methacryloyloxyethyl trimethylammonium chloride (75% solution in water) were mixed in a 2 liter glass reactor and purged with nitrogen and heated at 50° C. After 2 hours of purging, 10 grams of ammonium persulfate were added and the contents of the reactor were maintained at 50° C. for about 4 hours. The resulting solution was diluted with 300 grams of DI water.

In a separate reaction, 2.0 grams of PEHA and 0.93 gram of GTMACl (90% in water) were combined, and diluted with water to obtain a solution of total weight 50 grams. 26.66 grams of the thus prepared solution were added to 21.83 grams of glycidyl methacrylate-co-methacryloyloxyethyl trimethylammonium chloride solution (13.75% solution). To the mixture was added sufficient water to bring the total weight of the solution to 100 grams. The copolymer concentration in this coating solution was 3% by weight.

A 3 μm nominal pore size polyethersulfone membrane, SUPOR™ 3000, was immersed in the solution prepared above. The membrane was then cured in an oven at 95° C. for 0.5 hour. The membrane was then extracted in hot deionized water for 30 minutes and dried in an oven at 95° C.

Figure 2:
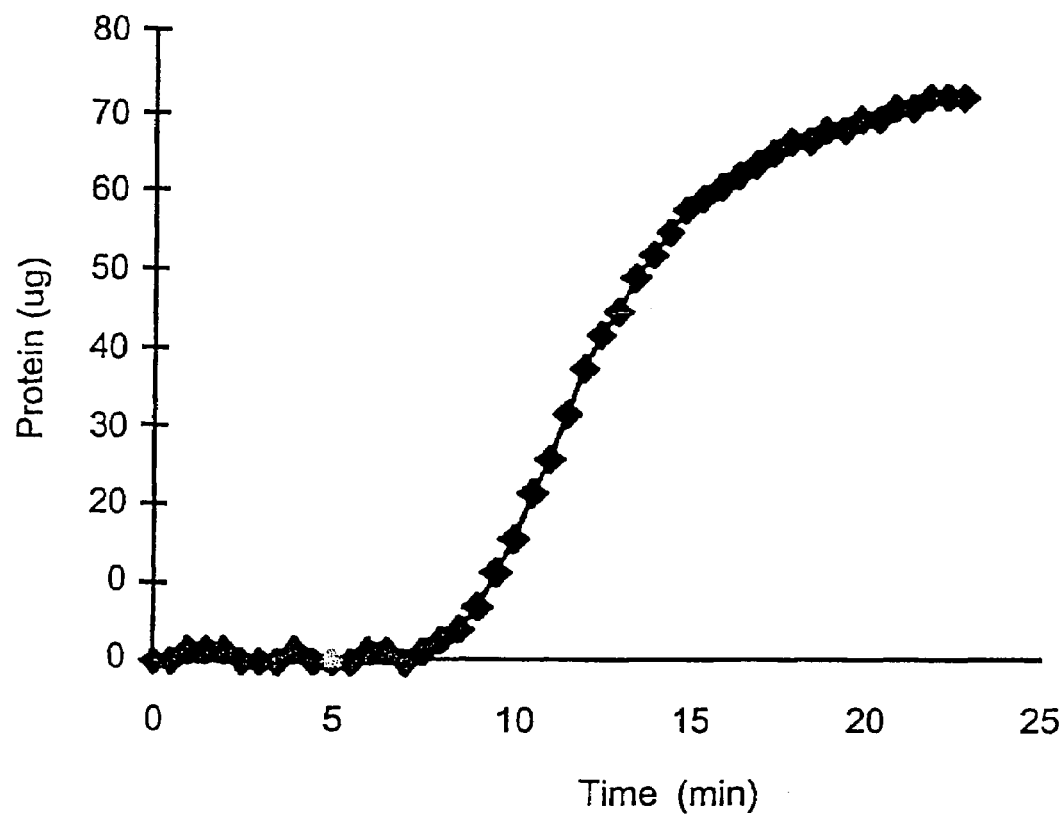
FIG. 2 depicts the breakthrough curve for BSA obtained on a membrane according to another embodiment of the present invention. The x-axis and the y-axis are as described in FIG. 1. See Example 5 for additional details.

The positively charged membrane prepared as above had a BSA binding capacity of 37.58 mg/ml, a water flow rate of 73 ml/min/cm$^2$, and a Metanil Yellow Dye absorption capacity of 480 ml. The breakthrough curve obtained on the membrane is shown in FIG. 2.

EXAMPLE 6

This Example illustrates a method of preparing still another embodiment of the positively charged membrane of the present invention. This Example further illustrates the properties of the prepared membrane. An acrylic polymer having epoxy groups and pendant cationic groups was prepared as follows.

A copolymer of glycidyl methacrylate and methacryloylaminopropyl trimethylammonium chloride was prepared as follows. 28.45 grams of glycidyl methacrylate-co-methacryloylaminopropyl trimethylammonium chloride (13.75% solution) and 26.60 grams of a solution of PEHA+GTMACl prepared as in Example 5 were mixed with sufficient amount of DI water to bring the total weight of the solution to 100 grams. The copolymer concentration in this coating solution was 3% by weight.

A 3 μm nominal pore size polyethersulfone membrane, SUPOR 3000, was immersed in the solution prepared above. The membrane was then cured in an oven at 95° C. for 0.5 hour. The membrane was then extracted in hot deionized water for 30 minutes and dried in an oven at 95° C.

The positively charged membrane prepared as above had a BSA binding capacity of 34 mg/ml, a water flow rate of 24 ml/min/cm$^2$, and a Metanil Yellow Dye absorption capacity of 90 ml.

EXAMPLE 7

This Example illustrates a method of preparing another embodiment of the positively charged membrane of the present invention. A PEI containing pendant cationic groups was prepared as follows. 8 grams of a 50% solution of branched PEI from Aldrich Chemical Company having an average molecular weight of 750,000 was combined with 10.4 g of a 90% solution in water of glycidyl trimethylammonium chloride (Fluka) in 181.2 g of deionized water. The resulting solution was agitated for about 15 minutes and then placed in a water bath at 36° C. for 16 hours. 0.4 gram of a 50% solution of ethyleneglycol diglycidylether was mixed with the solution containing the modified PEI prepared above to obtain a coating solution.

A hydrophilic polyethersulfone porous substrate sheet of nominal pore size of 0.8 μm was coated with the coating solution prepared above. The coated substrate was cured in an oven at 100° C. for a period of about 30 minutes. The cured membrane was extracted in boiling water for 1 hour to remove residues. The membrane obtained was tested for dye absorption and protein binding. The membrane had a Metanil Yellow Dye absorption capacity of 400 mL, and a specific BSA binding capacity of 47 mg.

EXAMPLE 8

Figure 3:
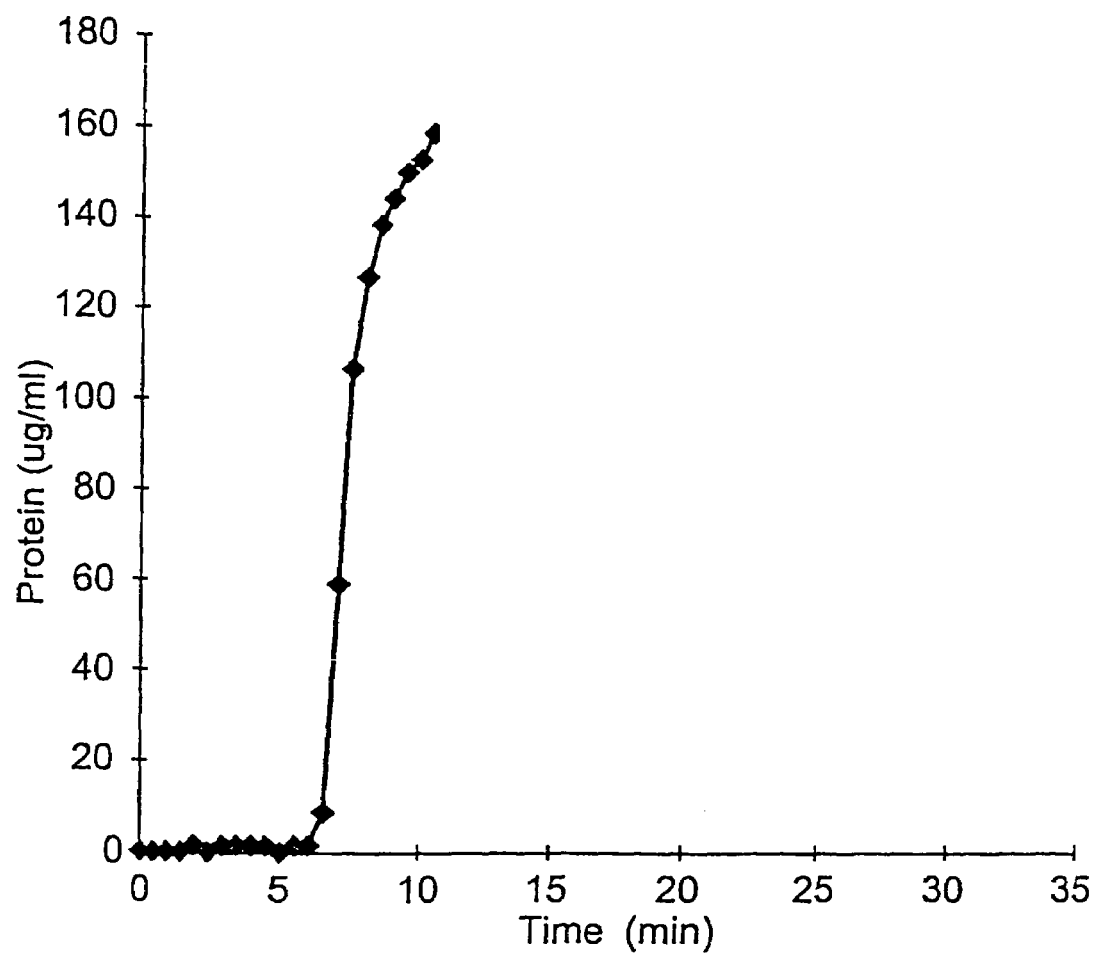
FIG. 3 depicts the breakthrough curve for bovine serum albumin (BSA) obtained on a membrane according to yet another embodiment of the present invention. The x-axis and the y-axis are as described in FIG. 1. See Example 8 for additional details.

This Example illustrates the capacity of an embodiment of the membrane of the present invention to bind proteins. Two membrane discs of effective filtration area of 2.9 cm$^2$, having a water flow rate of 40 ml/min/cm$^2$ at 10 psi, and prepared as in Example 7, were placed in a membrane test cell and a BSA solution containing 194.8 mg/ml of BSA in a 10 mM NaHPO$_4$ buffer at a pH of 7 was passed over the membranes at a flow rate of 4 ml/minute. Filtrate samples were collected and the BSA concentration was determined as a function of time. The results obtained are set forth in FIG. 3. The breakthrough curve depicted in FIG. 3 shows that the protein is retained on the membranes with great effectiveness for the first 6 minutes of filtration. Thus, the membranes were free of defects. Further, the slope of the breakthrough curve was nearly vertical. This vertical slope makes the membrane attractive for use in the separation of proteins present in a mixture since increased resolution is possible.

EXAMPLE 9

This Example illustrates a method of preparing another embodiment of the positively charged membrane of the present invention. This Example further illustrates the properties of that embodiment.

4.8 grams of a 50% solution of branched PEI from Aldrich Chemical Company having an average molecular weight of 50,000–100,000 were combined with 9.5 grams of a 90% solution in water of glycidyl trimethylammonium chloride (Fluka) and 184.7 grams of deionized water. The resulting solution was agitated for about 15 minutes and then placed in a water bath at 36° C. for 24 hours to obtain a solution containing a modified PEI. 1.0 gram of a 50% solution of ethyleneglycol diglycidylether (Aldrich) was mixed with the solution containing the modified PEI prepared above to obtain a coating solution.

A hydrophilic polyethersulfone porous substrate sheet of nominal pore size of 0.8 μm was coated with the coating solution prepared above. The coated substrate was cured in an oven at 100° C. for a period of about 30 minutes. The cured membrane was extracted in boiling water for 1 hour to remove residues. The membrane obtained was tested for dye absorption and protein binding. The membrane had a Metanil Yellow Dye absorption capacity of 350 mL, water flow rate of 50 ml/min/cm$^2$ at 24 inch Hg, and a specific BSA binding capacity of 44 mg/ml.

EXAMPLE 10

This Example illustrates a method of preparing yet another embodiment of the positively charged membrane of the present invention. This Example further illustrates the properties of that embodiment.

60 grams of a 50% solution of branched PEI from (Aldrich Chemical Company) having an average molecular weight of 750,000 were combined with 78 grams of a 90% solution in water of glycidyl trimethylammonium chloride and 362 grams of deionized water. The resulting solution was agitated for about 15 minutes and then placed in a water bath at 36° C. for 66 hours to obtain a modified PEI solution.

40 grams of the modified PEI solution were mixed with 59.08 grams of DI water and 0.5 grams of butyleneglycol diglycidyl ether. A hydrophilic polyethersulfone porous substrate sheet of nominal pore size of 0.8 μm was coated with the coating solution prepared above. The coated substrate was cured in an oven at 110° C. for a period of about 30 minutes. The cured membrane was extracted in boiling water for 0.5 hour to remove residues and dried in oven at 100° C. for 15 minutes. The membrane obtained was tested for water flow and protein binding. The membrane had a water flow of 37 ml/min/cm$^2$ and a specific BSA binding capacity of 44 mg/ml.

EXAMPLE 11

This Example illustrates a method of preparing another embodiment of the positively charged membrane of the present invention. This Example further illustrates the properties of that embodiment. In this preparation, (3-chloro-2-hydroxypropyl)trimethylammonium chloride was used as the PEI modifying agent instead of glycidyl trimethylammonium chloride. The modified PEI was prepared as follows.

24 grams of PEI (M.W. 750,000) (50% solution in water) were mixed with 54.4 grams of (3-chloro-2-hydroxypropyl) trimethylammonium chloride (60% solution in water) and 121.6 grams of DI water. The pH of the resulting solution was adjusted to 11 using 40% sodium hydroxide and the mixture was heated at 135° F. for about 16 hours to obtain a modified PEI solution.

25 grams of the modified PEI solution were mixed with 0.36 gram of ethyleneglycol diglycidylether and 24.64 grams of DI water. A hydrophilic polyethersulfone porous substrate sheet of nominal pore size of 0.8 μm was coated with the coating solution prepared above. The coated substrate was cured in an oven at 110° C. for a period of about 30 minutes. The cured membrane was extracted in boiling water for 0.5 hour to remove residues and dried in oven at 100° C. for 15 minutes. The membrane obtained was tested for water flow and protein binding. The membrane had a water flow rate of 40 ml/min/cm$^2$ and a specific BSA binding capacity of 31 mg/ml.

All references cited herein, including patents, patent applications, and publications, are incorporated by reference in their entireties.

While this invention has been described with an emphasis upon several embodiments, it will be obvious to those of ordinary skill in the art that variations of the embodiments may be used and that it is intended that the invention may be practiced otherwise than as specifically described herein. Accordingly, this invention includes all modifications encompassed within the spirit and scope of the invention as defined by the following claims.

What is claimed is:

1. A process for preparing a positively charged microporous membrane comprising a porous substrate and a crosslinked coating including a polymer backbone having pendant positively charged groups directly linked to the backbone through a polar spacer group by a single bond, the process comprising:
    (a) providing a porous substrate;
    (b) contacting the porous substrate with a coating composition comprising a polymer with a backbone having pendant positively charged groups directly linked to the backbone through a polar spacer group by a single bond and a crosslinking agent;
    (c) curing the substrate obtained in (b) to obtain the positively charged membrane; and
    (d) optionally, extracting the membrane obtained in (c) to remove extractable residue therein.

2. The process of claim 1, wherein the porous substrate is hydrophilic.

3. The process of claim 1, wherein the coating composition comprises a crosslinked polyamine.

4. The process of claim 1, wherein the coating composition includes a copolymer comprising diallylamine, a diallyldialkylammonium halide, an acrylic monomer having a quaternary ammonium group, and a crosslinking agent.

5. A positively charged microporous membrane comprising a porous substrate and a coating comprising a diallylamine copolymer having epoxy and pendant positively charged groups directly linked to the diallylamine copolymer through polar spacer groups, a polyalkyleneamine, and an amine reactive compound having a positively charged group, wherein the porous substrate is hydrophilic.

6. The positively charged microporous membrane of claim 5, wherein the diallylamine copolymer includes one or more nitrogen containing comonomers selected from the group consisting of diallyldimethylammonium chloride, dimethylaminopropyl methacrylamide, methacryloylaminopropyl trimethylammonium chloride, and combinations thereof.

7. The positively charged microporous membrane of claim 5, wherein the polyalkyleneamine comprises pentaethylenehexamine.

8. The positively charged microporous membrane of claim 5, wherein the diallylamine copolymer includes an acrylic monomer.

9. The positively charged microporous membrane of claim 8, wherein the diallylamine copolymer is prepared by a process comprising (a) polymerizing a mixture of diallylamine and methacryloylaminopropyl trimethylammonium chloride to obtain a polymer and (b) contacting the polymer obtained in (a) with epichlorohydrin.

10. The positively charged microporous membrane of claim 5, wherein the amine reactive compound is a glycidyl trialkylammonium halide.

11. The positively charged microporous membrane of claim 10, wherein the polyalkyleneamine comprises pentaethylenehexamine.

12. The positively charged microporous membrane of claim 11, wherein the coating includes a crosslinking agent.

13. The positively charged microporous membrane of claim 12, wherein the crosslinking agent is a polyglycidyl compound.

14. The positively charged microporous membrane of claim 5, wherein the porous substrate comprises a polymer.

15. The positively charged microporous membrane of claim 14, wherein the porous substrate comprises a polymer selected from the group consisting of polyaromatics, polysulfones, polyolefins, polystyrenes, polyamides, polyimides, polycarbonates, fluoropolymers, cellulosic polymers, and PEEK.

16. The positively charged microporous membrane of claim 15, wherein the porous substrate comprises a polysulfone.

* * * * *